United States Patent
Nagano et al.

(10) Patent No.: US 7,618,997 B2
(45) Date of Patent: *Nov. 17, 2009

(54) DIAMINOFLUORESCEIN DERIVATIVES

(75) Inventors: Tetsuo Nagano, 28-15, Amanuma 1-chome, Suginami-ku, Tokyo 167-0032 (JP); Hirotatsu Kojima, Tokyo (JP)

(73) Assignees: Sekisui Medical Co., Ltd., Tokyo (JP); Tetsuo Nagano, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/429,447

(22) Filed: May 8, 2006

(65) Prior Publication Data

US 2007/0117211 A1    May 24, 2007

Related U.S. Application Data

(60) Continuation of application No. 10/989,280, filed on Nov. 17, 2004, now abandoned, which is a continuation of application No. 10/412,300, filed on Apr. 14, 2003, now Pat. No. 6,833,386, which is a division of application No. 10/140,059, filed on May 8, 2002, now Pat. No. 6,569,892, which is a continuation of application No. 09/487,830, filed on Jan. 20, 2000, now Pat. No. 6,441,197.

(51) Int. Cl.
 *A61K 31/352* (2006.01)
(52) U.S. Cl. .................................... 514/455
(58) Field of Classification Search ................. 514/455
 See application file for complete search history.

(56) References Cited

U.S. PATENT DOCUMENTS

| | | | |
|---|---|---|---|
| 5,874,590 | A | 2/1999 | Nagano et al. |
| 6,201,134 | B1 | 3/2001 | Nagano et al. |
| 6,441,197 | B1 | 8/2002 | Nagano et al. |
| 6,569,892 | B2 | 5/2003 | Nagano et al. |
| 6,833,386 | B2 | 12/2004 | Nagano et al. |

FOREIGN PATENT DOCUMENTS

| | | |
|---|---|---|
| JP | 9-43153 | 2/1997 |
| JP | 10226688 | 8/1998 |

OTHER PUBLICATIONS

Abstract of 218th ACS National Meeting, Aug. 22-26, 1999.
Gendai Kagaku (Chemistry Today), pp. 23-30, Sep. 1999.
Pharmacia, 35, No. 10, pp. 1026-1030 (1999).
Kojima et al., "Fluorescent Indicators for Imaging Nitric Oxide Production", Angew: Chem. Int. Ed., 38, pp. 3209-3212 (1999).
Gendai Kagaku (Chemistry Today), pp. 25-29, Apr. 1994.
Palmer et al., "Nitric Oxide Release Accounts for the Biological Activity of Endothelium-Derived Relaxing Factor", Nature, 327, pp. 524-526, 1987.
Kelm et al., "Control of Coronary Vascular tone by Nitric Oxide", Circulation Research, 66, No. 6, pp. 1561-1575, 1990.
Shibuki, "An Electrochemical Microprobe for Detecting nitric Oxide Release in Brain Tissue", Neuroscience Research, 9, pp. 69-76, 1990.
Malinski et al., "Nitric Oxide Release from a Single Cell Measured in situ by a Porphyrinic-Based Microsensor", Nature, 356, pp. 676-678, 1992.
Green et al., "Analysis of Nitrate, Nitrite, and [$^{15}$N]Nitrate in Biological Fluids", Analytical Biochemistry, 126, pp. 131-138, 1982.
Entitled "Approach from the Latest Medicine 12, NO." edited by Noboru Toda, published by Medical View Co., Ltd., pp. 42-52, was published on Mar. 1995.
Archer, "Measurement of Nitric Oxide in Biological Models", FASEB Journal, 7, 349-360, 1993.
Stainton, "Simple, Efficient Reduction Column for Use in the Automated Determination of Nitrate in Water", Analytical Chemistry, 46, No. 11, p. 1616, 1974.
Sawicki et al., "Colorimetric Determination of Nitrate After Hydrazine Reduction to Nitrite", Microchemical Journal, 16, pp. 657-672, 1971.
Wiersma, "2,3-Diaminonaphthalene as a Spectrophotometric and Fluorometric Reagent for the Determination of Nitrite Ion", Analytical Letters, 3, No. 3, pp. 123-132, 1970.
Sawicki, "Fluorimetric Determination of Nitrate", Analytical Letters, 4, No. 11, pp. 761-775, 1971.
Damiani et al., "Fluorometric Determination of Nitrite", Talanta, 33, No. 8, pp. 649-652, 1986.
Misko et al., "A Fluorometric Assay for the Measurement of Nitrite in Biological Samples", Analytical Biochemistry, 214, pp. 11-16, 1993.
Doijn News, No. 74, Information, "A Reagent for the Determination of NO; 2,3-diaminonaphthalene," Dojindo Laboratories Inc., 1995.
Maeda et al., "Multiple Functions of Nitric Oxide in Pathophysiology and Microbiology: Analysis by a new Nitric Oxide Scavenger", Journal of Leukocyte Biology, 56, pp. 588-592, 1994.
Akaike et al., "Antagonistic Action of Imidazolineoxyl N-Oxides Against Endothelium-Derived Relaxing Factor/NO Through a Radical Reaction", Biochemistry, 32, pp. 827-832, 1993.
Organic Chemicals Catalog, 32, p. 1229, 1994, Tokyo Kasei Co., Ltd.
Hrabie, "New Nitric Oxide-Releasing Zwitterions Derived from Polyamines", J. Org. Chem., 58, pp. 1472-1476, 1993.
Kikuchi et al., "Novel Detection Method of Nitric Oxide Using Horseradish Peroxidase", Biol. Pharm. Bill., 19, pp. 649-651, 1996.
Abstract of 119th Annual Meeting of the Pharmaceutical Soicety of Japan, p. 62, is from a meeting that was conducted on Aug. 22-26, 1999 in New Orleans, LA.

*Primary Examiner*—Taofiq A Solola
(74) *Attorney, Agent, or Firm*—Greenblum & Bernstein, P.L.C.

(57) ABSTRACT

A compound represented by the following formula (I):

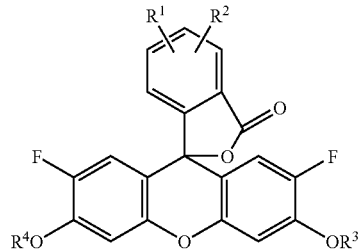

wherein $R^1$ and $R^2$ represent amino groups that substitute at adjacent positions on the phenyl ring, provided that either of $R^1$ and $R^2$ represents a mono($C_{1-6}$ alkyl)-substituted amino group and the other represents an unsubstituted amino group; and $R^3$ and $R^4$ independently represent hydrogen atom or an acyl group, and an agent for measurement of nitrogen monoxide which comprises said compound.

16 Claims, 4 Drawing Sheets

DIAMINOFLUORESCEIN DERIVATIVES

CROSS-REFERENCE TO RELATED APPLICATIONS

This application is a continuation of application Ser. No. 10/989,280, filed Nov. 17, 2004, now abandoned which is a continuation of application Ser. No. 10/412,300, filed Apr. 14, 2003, now U.S. Pat. No. 6,833,386 which is a divisional of application Ser. No. 10/140,059, filed May 8, 2002, now U.S. Pat. No. 6,569,892 B2, which is a continuation of application Ser. No. 09/487,830, filed Jan. 20, 2000, now U.S. Pat. No. 6,441,197 B1. The entire disclosures of application Ser. Nos. 10/989,280, 10/412,300, 10/140,059 and 09/487,830 are considered as being part of the disclosure of this application, and the entire disclosure of application Ser. Nos. 10/989,280, 10/412,300, 10/140,059 and 09/487,830 are expressly incorporated by reference herein in their entireties.

FIELD OF THE INVENTION

The present invention relates to fluorescein derivatives which are useful as agents for measurement of nitrogen monoxide. It also relates to agents for measuring nitrogen monoxide which comprise said compound.

RELATED ART

Nitrogen monoxide (NO) is an unstable radical having a short life, and it has been elucidated that nitrogen monoxide has important functions as a physiologically active substance in a living body (featured in Gendai Kagaku (Chemistry Today), April, 1994). Methods for measuring nitrogen monoxide are mainly classified into indirect methods where oxidative degradation products of nitrogen monoxide such as $NO_2^-$ or $NO_3^-$ are measured, and methods where nitrogen monoxide is directly measured. The direct methods have been focused from the standpoint that they achieve detection and quantification of nitrogen monoxide under physiological condition. However, no measuring method has been developed to date that has sufficient specificity and high sensitivity and is applicable to an in vitro system.

For example, a chemiluminescence method which utilizes luminescence emitted during an ozonic oxidation of NO radicals (Palmer, R. M., et al., Nature, 327, pp. 524-526, 1987); a method which comprises the step of measuring an absorption spectrum of metHb that is produced by an oxidation of oxy-hemoglobin ($O_2Hb$) (Kelm, M., et al., Circ. Res. 66, pp. 1561-1575, 1990); a method which comprises the step of measuring electric current generated during an oxidation by means of electrodes that are inserted into a tissue (Shibuki, K., Neurosci. Res. 9, pp. 69-76, 1990; Malinski, T., Nature, 356, pp. 676-678, 1992); and the Griess reaction method (Green, L. C., et al., Anal. Biochem., 126, pp. 131-138, 1992) are known as typical methods (as reviews, see, "3. Method for measurement of NO," by Tetsuo Nagano, pp. 42-52, "Approach from the Latest Medicine 12, NO" edited by Noboru Toda, published by Medical View Co., Ltd.; and Archer, S., FASEB J., 7, pp. 349-360, 1993).

The Griess reaction method comprises a detection step that utilizes azo coupling between naphthylethylenediamine and a diazonium salt compound formed with $NO_2^-$ which is generated by the oxidation of nitrogen monoxide radicals. This method is advantageous because it does not require particular apparatuses or techniques, although nitrogen monoxide radicals are not directly measured by the method. In addition, $NO_3^-$ can also be measured after being reduced to $NO_2^-$ by using cadmium (Stainton, M. P., Anal. Chem., 46, p. 1616, 1974; Green, L. C., et al., Anal. Biochem., 126, pp. 131-138, 1982) or hydrazine (Sawicki, C. R. and Scaringelli, F. P., Microchem. J., 16, pp. 657-672, 1971), and accordingly, the method also has characteristic feature that it enables the measurement of metabolites related to nitrogen monoxide.

2,3-Diaminonaphthalene has also been known as an agent for measuring nitrogen monoxide by detecting $NO_2^-$ as in a similar manner to Griess reaction method. This agent reacts with $NO_2^-$ under an acidic condition to form a fluorescent adduct, i.e., naphthalenetriazole (chemical name: 1-[H]-naphtho[2,3-d]triazole) (Wiersma, J. H., Anal. Lett., 3, pp. 123-132, 1970). Details of the reaction conditions of 2,3-diaminonaphthalene and $NO_2^-$ have been studied, and it has been found that the reaction proceeds most rapidly at a pH not higher than 2, and completes in about 5 minutes at room temperature (Wiersma, J. H., Anal. Lett., 3, pp. 123-132, 1970; Sawicki, C. R., Anal. Lett., 4, pp. 761-775, 1971). The resulting adduct emits fluorescence most efficiently at a pH not lower than 10 (Damiani, P. and Burini, G., Talanta, 8, pp. 649-652, 1986).

The method for measuring nitrogen monoxide using the above 2,3-diaminonaphthalene has characteristic features of 50- to 100-fold higher sensitivity compared to the Griess reaction method, since its detection limit is as low as approximately several tens nM (Misko, T. P., Anal. Biochem. 214, pp. 11-16, 1993). This method is highly advantageous because it needs no particular apparatus or technique and can be carried out conveniently (as a review of the aforementioned method, see, DOJIN News. No. 74, Information, "An agent for the determination of NO: 2,3-diaminonaphthalene," Dojindo Laboratories Inc., 1995). However, the method does not utilize nitrogen monoxide, per se, but utilizes an oxidation product, i.e., $NO_2^-$, as a reactant. Accordingly, the method is considered as an indirect method when compared to those including direct measurement of nitrogen monoxide. Furthermore,, because the reaction of 2,3-diaminonaphthalene with $NO_2^-$ is carried out under a strongly acidic condition (pH not higher than 2), the method has a problem in that it cannot be employed for detection or quantification of nitrogen monoxide under a physiological condition.

The inventors of the present invention conducted researches to provide a means that enables direct and highly sensitive measurement of nitrogen monoxide under a physiological condition, and as a result, they found that nitrogen monoxide can efficiently react with 2;3-diaminonaphthalene or its derivatives, even under a neutral condition, in the presence of an oxygen source such as dissolved oxygen or oxide compounds (e.g., PTIO and derivatives thereof such as carboxy-PTIO), and a fluorescent naphthalenetriazole or a derivative thereof is obtained. They also found that a method for measuring nitrogen monoxide utilizing the above reaction has extremely high detection sensitivity, and can achieve accurate quantification of very small amount of nitrogen monoxide (see, the specification of Japanese Patent Application No. Hei 7-189978).

However, the aforementioned method utilizing 2,3-diaminonaphthalene requires the irradiation with excitation light having a short wavelength of approximately 370-390 nm for the detection of fluorescence, and this may cause damages to cells and/or tissues in a measurement system. Strong autofluorescence of cells, per se, may, also possibly affect the measurement, and moreover, there is a problem that a fluorescence filter provided on a usual fluorescence microscope fails to sufficiently cut off excitation light during fluorescence measurement. In addition, the fluorescent triazole compound formed from 2,3-diaminonaphthalene has rather insufficient fluorescence intensity, and therefore, it is difficult to achieve accurate measurement of intracellular fluorescence of an individual cell by ordinary fluorescence microscopy. Since 2,3-diaminonaphthalene itself has a simple chemical structure, there is also a problem that the compound is not suitable as a fundamental structure for various chemical modifications so as to achieve intracellular localization of an agent.

As a method for measuring nitrogen monoxide that solved these problems, the inventors of the present invention proposed a method utilizing a class of diaminofluorescein derivatives (U.S. Pat. No. 5,874,590). By using the derivatives, nitrogen monoxide can be measured with an excitation light having a long wavelength that gives no damage to living tissues or cells, and intracellularly existing nitrogen monoxide can be accurately measured for each individual cell. The diaminofluorescein derivatives are extremely satisfactory agents from the standpoints of reactivity with nitrogen monoxide and measurement sensitivity. However, the derivatives have a problem that the fluorescence intensity of the triazole derivatives produced through the reaction with nitrogen monoxide slightly increases in the weakly basic to weakly acidic region. Moreover, the triazole compounds also have a problem of instability to light. For these reasons, it has been desired to develop an agent for measurement of nitrogen monoxide that gives no change in fluorescence intensity due to alteration in pH, and produces a fluorescent substance that is stable to light.

DISCLOSURE OF THE INVENTION

An object of the present invention is to provide compounds which are useful for measurement of nitrogen monoxide. More specifically, the object of the present invention is to provide compounds that enable the measurement of nitrogen monoxide by means of excitation light having a long wavelength which does not cause damages to living tissues and cells, and can efficiently react with nitrogen monoxide under a neutral condition to provide a fluorescent substance having excellent fluorescence intensity, which fluorescent substance has stability to light and whose fluorescence intensity is not affected by alteration in pH.

Another object of the present invention is to provide an agent for measuring nitrogen monoxide which comprises a compound having the aforementioned characteristic features. More specifically, the object is to provide an agent for measuring nitrogen monoxide which enables accurate measurement of intracellularly existing nitrogen monoxide for individual cells.

The inventors of the present invention made efforts to achieve the foregoing objects, and as a result, they found that a particular class of fluorescein derivatives, which themselves emit almost no fluorescence, can easily react with nitrogen monoxide under a neutral condition, and give triazole compounds having high fluorescence intensity. They also found that the triazole derivatives can emit strong fluorescence at approximately 515 nm when irradiated with excitation light having a longer wavelength of about 495 nm, and that the derivatives gave substantially no change in fluorescence intensity from weakly basic to weakly acidic regions and the derivatives were stable to light. They further found that intracellular nitrogen monoxide concentrations in individual cells were accurately and conveniently measurable by using these compounds as an agent for measuring nitrogen monoxide.

The present invention was achieved on the basis of these findings.

The present invention thus provides a compound represented by the following formula (I):

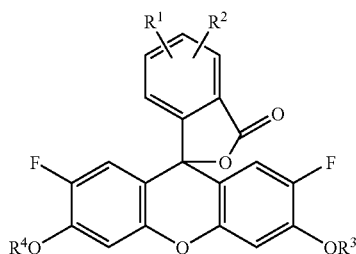

wherein $R^1$ and $R^2$ represent amino groups that substitute at adjacent positions on the phenyl ring, provided that either of $R^1$ and $R^2$ represents a mono($C_{1-6}$ alkyl)-substituted amino group and the other represents an unsubstituted amino group; and $R^3$ and $R^4$ independently represent hydrogen atom or an acyl group.

According to preferred embodiments of the present invention, there are provided the aforementioned compound wherein the monoalkyl-substituted amino group represented by either of $R^1$ and $R^2$ is a monomethylamino group; and the aforementioned compound wherein both of $R^3$ and $R^4$ represent hydrogen atom.

According to another aspect of the present invention, there is provided an agent for measurement of nitrogen monoxide which comprises the aforementioned compound.

According to further aspect of the present invention, there is provided a compound represented by the following formula (II):

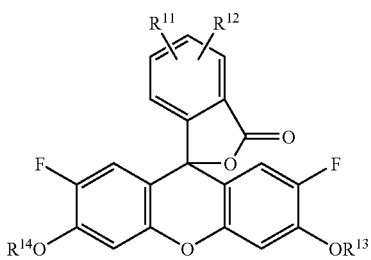

wherein $R^{11}$ and $R^{12}$ combine together to form a group represented by —N═N—N($R^{19}$)— which forms a ring structure at adjacent positions on the phenyl ring, wherein $R^{19}$ represents a $C_{1-6}$ alkyl group, or $R^{11}$ and $R^{12}$ represent a combination of an amino group and a nitro group which substitute at adjacent positions on the phenyl ring; and $R^{13}$ and $R^{14}$ independently represent hydrogen atom or an acyl group.

The present invention further provides a method for measuring nitrogen monoxide which comprises the steps of:
(1) reacting a compound represented by the above formula (I) with nitrogen monoxide; and
(2) detecting a compound of the formula (II) formed by the above step (1).

BEST MODE FOR CARRYING OUT THE INVENTION

Figure 1:
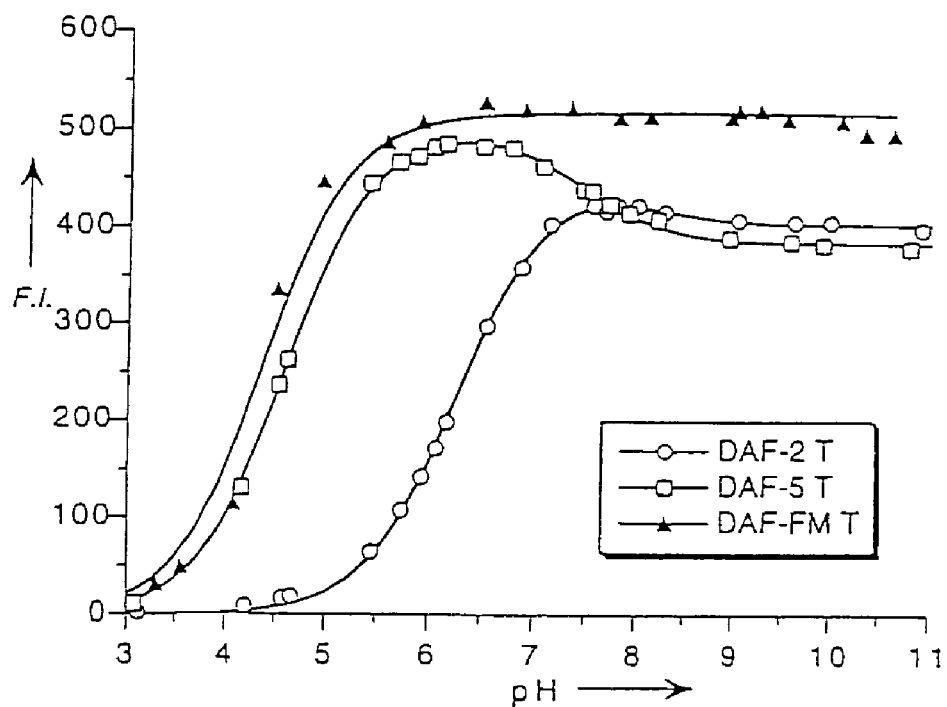
FIG. 1 shows changes in fluorescence intensity of the triazole derivatives disclosed in U.S. Pat. No. 5,874,590 (DAF-2T and DAF-5T) and DAF-FM T due to alteration in pH.

In the above general formula (I), $R^1$ and $R^2$ represent amino groups which substitute at adjacent positions on the phenyl ring. Either of $R^1$ and $R^2$ represents a mono($C_{1-6}$ alkyl)substituted amino group, and the other represents an unsubstituted amino group. The $C_{1-6}$ alkyl group constituting the mono($C_{1-6}$ alkyl)substituted amino group may be straight or branched. More specifically, methyl group, ethyl group, n-propyl group, isopropyl group, n-butyl group, sec-butyl group, tert-butyl group and the like may be used. Other $C_{1-6}$ alkyl groups or $C_{1-6}$ alkyl moieties of functional groups containing a $C_{1-6}$ alkyl moiety, which are referred to in the specification, may be similar to those explained above.

$R^3$ and $R^4$ independently represent hydrogen atom or an acyl group. Examples of the acyl group include, for example, an arylcarbonyl group such as benzoyl group, p-methoxybenzoyl group, p-chlorobenzoyl group, or naphthylcarbonyl group; a $C_{1-6}$ alkylcarbonyl group such as acetyl group, propionyl group, or butanoyl group and the like. Preferably, $R^3$ and $R^4$ are independently hydrogen atom or an acetyl group, and most preferably, both of $R^3$ and $R^4$ are hydrogen atoms or both are acetyl groups.

In the aforementioned formula (II), $R^{11}$ and $R^{12}$ combine together to represent the group —N=N—N($R^{19}$)— which forms a ring structure at adjacent positions on the phenyl ring. $R^{19}$ represents a $C_{1-6}$ alkyl group. $R^{11}$ and $R^{12}$ also represent a combination of an amino group and a nitro group which substitute at adjacent positions on the phenyl ring, wherein either of $R^{11}$ and $R^{12}$ represents an amino group and the other represents a nitro group. The amino group represented by $R^{11}$ or $R^{12}$ may be unsubstituted, or may have one $C_{1-6}$ alkyl group. The amino group may have an acyl group such as acetyl group, trifluoroacetyl group, or benzoyl group, or a protective group such as alkylsilyl groups including trimethylsilyl group. An arylalkyl group such as benzyl group may also be used as the protective group.

$R^{13}$ and $R^{14}$ independently represent hydrogen atom or an acyl group. As the acyl group, for example, an arylcarbonyl group such as benzoyl group, p-methoxybenzoyl group, p-chlorobenzoyl group, or naphthylcarbonyl group; a $C_{1-6}$ alkylcarbonyl group such as acetyl group, propionyl group, or butanoyl group and the like may be used. Preferably, $R^{13}$ and $R^{14}$ independently represent hydrogen atom or acetyl group, and most preferably, both of $R^{13}$ and $R^{14}$ are hydrogen atoms or acetyl groups.

The compounds of the formula (I) and the formula (II) wherein $R^{11}$ and $R^{12}$ represent the combination of an amino group and a nitro group substituting at adjacent positions on the phenyl ring can be prepared, for example, according to the methods described in U.S. Pat. No. 5,874,590, and the details of the methods will be specifically explained in the example section of the specification. It will be understood that the compounds of the formula (II) are useful as synthetic intermediate compounds for the preparation of the compounds of the formula (I). Among the compounds represented by the formula (II), those wherein $R^{11}$ and $R^{12}$ combine together to represent the group —N=N—N($R^{19}$)— that forms a ring structure at adjacent positions on the phenyl ring can be prepared by reacting the compounds of the aforementioned formula (I) with nitrogen monoxide. These compounds are highly fluorescent as explained later, and are useful for the measurement of nitrogen monoxide.

By referring to the methods for preparation of the fluorescein derivatives described in the aforementioned publication and specific explanations in the examples, one of ordinarily skilled artisan will readily understand that the compounds falling within the scope of the formula (I) and the formula (II) can easily be prepared. Methods for preparing fluorescein derivatives having variety of substituents are known, and therefore, those skilled in the art can readily prepare any compounds that fall within the formula (I) and (II) by combining known methods available to skilled artisan with the methods disclosed in the examples of the specification.

The compounds of the formula (I) and the formula (II) according to the present invention may have one or more asymmetric carbon atoms. Any optical isomers of the compounds based on one or more asymmetric carbon atoms which are optically pure forms, any mixtures of the optical isomers, racemates, diastereoisomers in pure forms, mixtures of the diastereoisomers and the like fall within the scope of the present invention. The compounds of the formula (I) and the formula (II) of the present invention may exist as base addition salts such as sodium salts or potassium salts, or acid addition salts such as hydrochlorides, sulfates, or p-toluenesulfonates. Any one of these salts also falls within the scope of the present invention. Furthermore, the compounds of the present invention in free form or in the form of a salt may exist as hydrates or solvates, and it should be understood that they also fall within the scope of the present invention, and they can be utilized as the agent for measurement of the present invention.

Fluorescein derivatives are known to exist also as compounds without the formation of a lactone ring, i.e., 9-(o-carboxyphenyl)-6-hydroxy-3H-xanthen-3-one derivatives. The compounds of the present invention may also exist in the form of the aforementioned structural isomer, and it will be readily understood by those skilled in the art that they also fall within the scope of the present invention. In the formulas (I) and (II), and in the schemes set out above, only compounds having a lactone ring are shown for convenience.

Thus, the present invention is also directed to a compound represented by the following formula (I'):

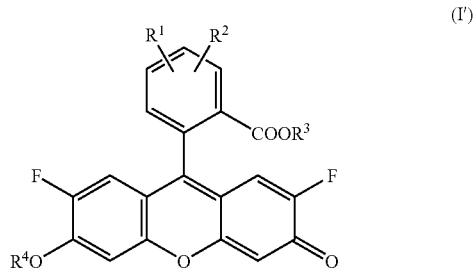

wherein $R^1$ and $R^2$ represent amino groups that substitute at adjacent positions on the phenyl ring, provided that either of $R^1$ and $R^2$ represents a mono($C_{1-6}$ alkyl)-substituted amino group and the other represents an unsubstituted amino group and wherein $R^3$ represents hydrogen atom or an alkyl group and $R^4$ represents hydrogen atom or an acyl group. Moreover, the monoalkyl-substituted amino group represented by either of $R^1$ and; $R^2$ can be a monomethylamino group, and both of $R^3$ and $R^4$ can represent hydrogen atoms.

Moreover, the present invention is also directed to a compound represented by the following formula (II'):

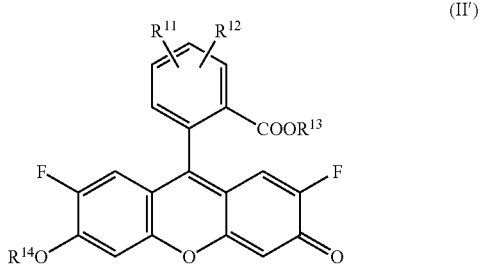

(II')

wherein $R^{11}$ and $R^{12}$ combine together to form a group represented by —N=N—N($R^{19}$)—which forms a ring structure at adjacent positions on the phenyl ring, wherein $R^{19}$ represents a $C_{1-6}$ alkyl group, or $R^{11}$ and $R^{12}$ represent a combination of an amino group and a nitro group which substitute at adjacent positions on the phenyl ring; and $R^{13}$ represents hydrogen atom or an alkyl group, and $R^{14}$ represents hydrogen atom or an acyl group.

Still further, the present invention is directed to a method for measuring nitrogen monoxide which comprises:

reacting a compound represented by formula (I') with nitrogen monoxide to form a compound represented by formula (II');

irradiating the compound represented by formula (II') with light to cause fluorescence of the irradiated compound; and measuring the fluorescence;

wherein the compound represented by formula (I') has the following formula:

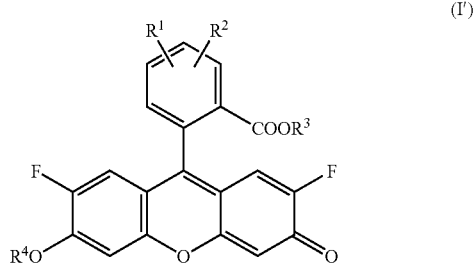

(I')

wherein $R^1$ and $R^2$ represent amino groups that substitute at adjacent positions on the phenyl ring, provided that either of $R^1$ and $R^2$ represents a mono($C_{1-6}$ alkyl)-substituted amino group and the other represents an unsubstituted amino group and wherein $R^3$ represents hydrogen atom or an alkyl group and $R^4$ represents hydrogen atom or an acyl group; and wherein the compound represented by formula (II') has the following formula:

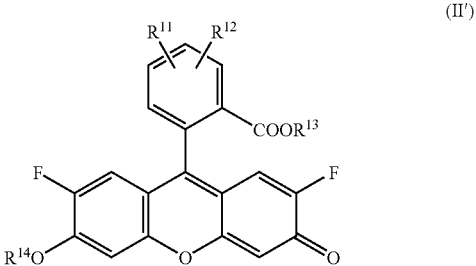

(II')

wherein $R^{11}$ and $R^{12}$ combine together to form a group represented by —N=N—N($R^{19}$)—which forms a ring structure at adjacent positions on the phenyl ring, wherein $R^{19}$ represents a $C_{1-6}$ alkyl group, or $R^{11}$ and $R^{12}$ represent a combination of an amino group and a nitro group which substitute at adjacent positions on the phenyl ring; and $R^{13}$ represents hydrogen atom or an alkyl group, and R represents hydrogen atom or an acyl group.

The compounds represented by the formula (I) of the present invention have a characteristic property that they efficiently react with nitrogen monoxide under a neutral condition and provide compounds of the formula (II) wherein $R^{11}$ and $R^{12}$ combine together to form the group of —N=N—N($R^{19}$)—which forms a ring structure at adjacent positions on the phenyl ring. The compounds represented by the formula (I), per se, emit almost no fluorescence when irradiated with excitation light of 495 nm under a neutral condition, whereas the compounds of the above formula (II) have a property of emitting extremely strong fluorescence (emission: 515 nm) under the same condition. Therefore, nitrogen monoxide in a living tissue or a cell can be measured by introducing the compound represented by the formula (I) into a living tissue or a cell to allow the compound react with nitrogen monoxide to form the fluorescent compound represented by the above formula (II), and then measuring fluorescence of said compound. The compounds of the formula (II) formed as described above have an excellent property that they give substantially no change in fluorescence intensity from a weakly basic region of about pH 9 to a weakly acidic region of about pH 6.

The method for measurement of nitrogen monoxide provided by the present invention comprises the steps of reacting a compound represented by the above formula (I) with nitrogen monoxide to form a compound of formula (II), and then measuring fluorescence of the compound of the formula (II). The term "measurement" used in the specification should be construed in its broadest sense, which includes measurements for variety of purposes such as, for example, detection, quantification, qualitative analysis and the like. The above reaction can preferably be carried out under a neutral condition, for example, in the range of from pH 6.0 to 8.0, preferably in the range of from pH 6.5 to 7.8, and more preferably in the range of from pH 6.8 to 7.6. However, the measurements of nitrogen monoxide according to the present invention are not limited to those conducted under the neutral range. For example, measurements can also be performed under a strongly acidic condition such as in gastric mucosal cells.

The compounds wherein $R^3$ and $R^4$ are acetyl groups can easily pass through cellular membranes so as to be taken intracellularly, and then they are converted into the compounds wherein $R^3$ and $R^4$ are hydrogen atoms after the hydrolysis of the ester of the acetoxy groups. The resulting dihydroxy compound are highly hydrophilic, and not easily excreted extracellularly from the intracellular environment. Accordingly, the compound wherein R and $R^4$ are acetyl groups are useful as an agent for measurement, per se, but useful as a so-called pro-drug for intracellularly transporting the measuring agent (the compound wherein $R^3$ and $R^4$ are hydrogen atoms) at a high concentration.

The measurement of fluorescence can be carried out according to a known fluorometry method (see, for example, Wiersma, J. H., Anal. Lett., 3, pp. 123-132, 1970; Sawicki, C. R., Anal. Lett., 4, pp. 761-775, 1971; Damiani, P. and Burini, G., Talanta, 8, pp. 649-652,;1986; Damiani, P. and Burini, G., Talanta, 8, pp. 649-652, 1986; and Misko, T. P., Anal. Biochem., 214, pp. 11-16, 1993). For the nitrogen monoxide measurement according to the present invention, for example, irradiation with light of about 495 nm as excitation light, and measurement of fluorescence of about 515 nm may preferably be performed. By using the light having such wavelength, efficient cut off can be achieved by using a fluorescence filter provided on an ordinary fluorescence microscope, and measurement with high 67 can be performed without using a special filter.

Where particularly high sensitive measurement is required, the aforementioned measurement of nitrogen monoxide may be carried out in the presence of an oxygen source. As the oxygen source, for example, oxygen, ozone, oxide compounds or the like can be used. As the oxygen, dissolved oxygen can generally be used, and if desired, oxygen gas may be introduced into the reaction system or an agent that can generate oxygen (e.g., hydrogen peroxide) may be added. The oxide compounds are not particularly limited so long as they have an oxide bond that can easily be cleaved to release oxygen, e.g., N—O, S—O, or P—O. For example, PTIO (2-phenyl-4,4,5,5-tetramethylimidazoline-1-oxyl-3-oxide, Maeda, H., et al., J. Leuk. Biol., 56, pp. 588-592, 1994; and Akaike, T., et al., Biochemistry, 32, pp. 827-832, i1993) or derivatives thereof (carboxy-PTIO which has carboxyl group introduced at the para-position of the phenyl group of PTIO), triphenylphosphine oxide, triethylamine oxide or the like can be used.

Among the oxide compounds mentioned above, PTIO and derivatives thereof (e.g., carboxy-PTIO) are particularly preferred compounds, and they can be readily obtained by those skilled in the art (listed in, for example, Organic Chemicals Catalog, 32, 1994, Tokyo Kasei Co., Ltd.). The oxide compounds, per se, may be used as a reagent, or those encapsulated in liposomes or the like may also be used. Although the amount of the oxygen source is not particularly limited, preferable amount may be at least 1 μmol or more, preferably 10-30 μmol, and more preferably about 10-20 μmol based on nitrogen monoxide to be measured. For measurement of samples from a living body, from 10 to 20 μmol of the oxide compound may preferably be added to the samples. However, a required amount of the oxygen source is generally supplied by dissolved oxygen. If the amount of oxygen source is extremely small, measuring sensitivity may sometimes be lowered, and if an extremely large amount of oxygen source exists, emission of fluorescence may be disadvantageously affected. Therefore, it is preferred that an amount of nitrogen monoxide to be measured is predicted by a preliminary experiment or a known method so that the oxygen source within an appropriate concentration range can be applied. The reaction can be carried out at a temperature of from 10° C. to 25° C.

EXAMPLES

The present invention will be further explained more specifically by way of the following examples. However, the scope of the present invention is not limited to these examples. Synthetic scheme of Example 1 is shown below.

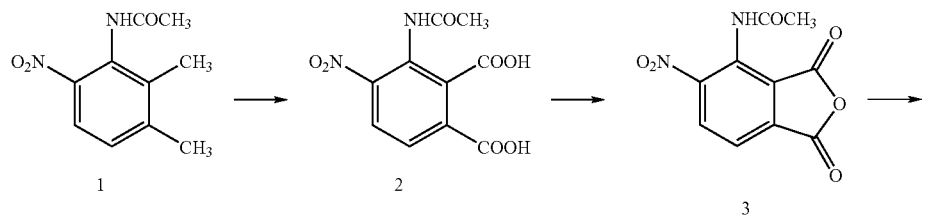

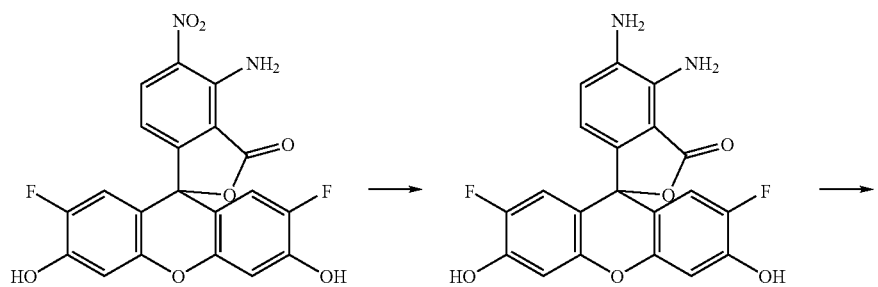

-continued

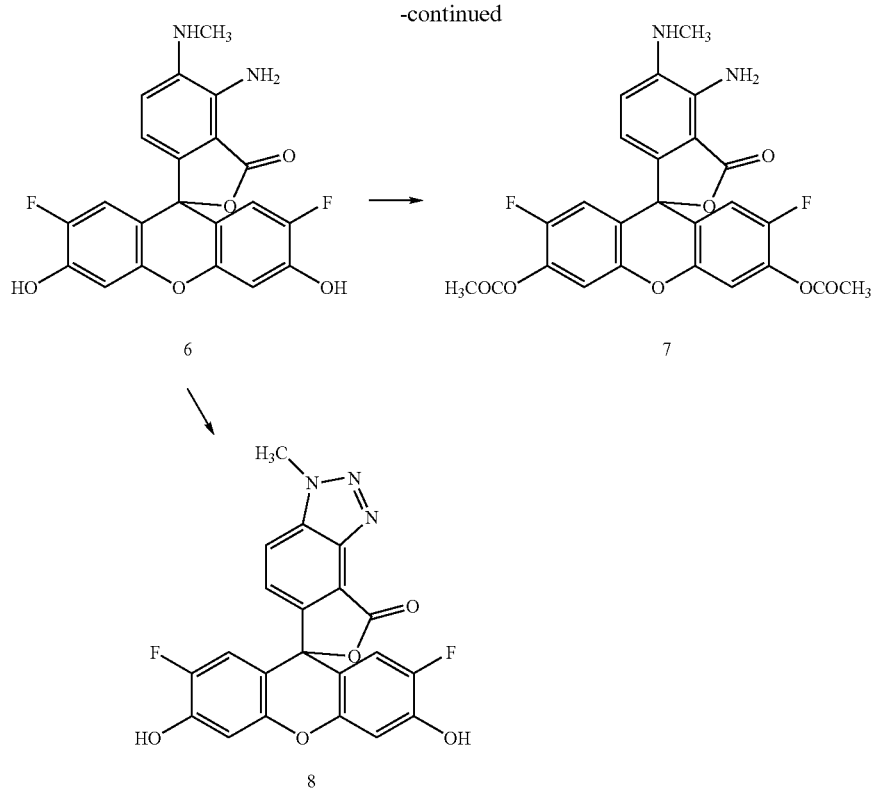

Example 1

Preparation of 4-amino-5-(N-methylamino)-2',7'-difluoro-3',6'-dihydroxy-spiro[isobenzofuran-1(3H),9'-[9H]xanthen]-3-one DAF-FM)

(a) 2,3-Dimethyl-6-nitroacetanilide (1)

2,3-Dimethyl-6-nitroaniline (25.3 g, 0.152 mol) was dissolved in acetic acid (290 ml), and the solution was added with acetic anhydride (15 ml, 0.159 mol) and refluxed for 1 hour. After the solvent was evaporated, the residue was recrystallized from ethanol to obtain the title compound (29.3 g, 98%).

$^1$H-NMR (300 MHz, CDCl$_3$) δ 2.18 (3H, s); 2.24 (3H, s); 2.39 (3H, s); 7.18 (1H, d, J=8.3 Hz); 7.80 (1H, d, J=8.3Hz); 8.46 (1H, s)

(b) 3-Acetamide-4-nitrophthalic acid (2)

2,3-Dimethyl-6-nitroacetanilide (29.2 g, 0.140 mol) was suspended in water (1 liter), and the suspension was added with MgSO$_4$ (100 g, 0.831 mol) and refluxed, and then added with KMnO$_4$ (133 g, 0.841 mol) suspended portionwise in water (2 liters in total). The hot reaction mixture was filtered, and the filtrate was added and saturated with sodium chloride. After cooling, the mixture was acidified with cold HCl, and precipitates were collected by filtration. The filtrate was extracted with ethyl acetate, and the solvent was evaporated to obtain the title compound (19.6 g, 52%).

$^1$H-NMR (300 MHz, DMSO-d$_6$) δ 1.97 (3H, s); 7.90 (1H, d, J=8.4Hz); 8.04 (1H, d, J=8.4Hz); 10.13 (1H, s); 13.5 (2H, br)

(c) 3-Acetamido-4-nitrophthalic anhydride (3)

3-Acetamido-4-nitrophthalic acid (0.538 g, 2.00 mmol) was dissolved in acetic anhydride (10 ml) at 80° C., and the solution was added with acetyl chloride (1 ml) and stirred for 2 hours. The solvent was evaporated, and a small amount of anhydrous dichloromethane was added to the residue, and precipitates were collected by filtration to obtain the title compound (0.29 g, 58%).

$^1$H-NMR (300 MHz, CDCl$_3$) δ 2.35 (3H, s); 7.89 (1H, d, J=8.2 Hz); 8.45 (1H, d, J=8.2 Hz); 9.01 (1H, s)

(d) 4-Amino-5-nitro-2',7'-difluoro-3',6'-dihydroxy-spiro[isobenzofuran-1(3H),9'-[9H]xanthen]-3-one (4: 3-amino-4-nitrodifluorofluorescein)

3-Acetamido-4-nitrophthalic anhydride (1.3 g, 5.0 mmol) and 4-fluororesorcinol (1.3 g, 10 mmol) were added to methanesulfonic acid (10 ml), and the mixture was stirred at 80° C. under an argon atmosphere for 60 hours. The reaction mixture was added with water (120 ml) and refluxed for 2 hours. The reaction mixture was adjusted to pH 2, and precipitates were collected by filtration. The obtained product was dried and purified by silica gel chromatography (3% methanol/97% dichloromethane, v/v) to obtain the title compound (1.3 g, 61%).

$^1$H-NMR (300 MHz, DMSO-d$_6$) δ 6.40 (d, 1H, J=8.6); 6.87 (d, 2H, J=7.3 Hz); 6.89 (d, 2H, J=11.3 Hz); 7.95 (br, 2H); 8.36 (d, 1H, J=8.6 Hz); 10.8 (br, 2H)

(e) 4,5-Diamino-2',7'-difluoro-3',6'-dihydroxy-spiro[isobenzofuran-1(3H),9'-[9H]-xanthen]-3-one (5: 3,4-diaminodifluorofluorescein) (DAF-7)

4-Amino-5-nitro-2',7'-difluoro-3',6'-dihydroxy-spiro[isobenzofuran-1(3H),9'-[9H]xanthen]-3-one (1.3 g, 3.0mmol) was added to an aqueous solution of $Na_2S$ and NaSH, and the mixture was refluxed for 24 hours. The reaction mixture was cooled, and adjusted to pH 3 with hydrochloric acid, and precipitates were collected by filtration. The obtained product was dried and purified by silica gel chromatography to obtain the title compound (0.94 g, 78%).

$^1$H-NMR (300 MHz, DMSO-$d_6$) δ 5.10 (s, 2H); 5.94 (s, 2H); 6.11 (d, 1H, J=7.9Hz); 6.48 (d, 2H, J=11.3Hz); 6.81 (d, 1H, J=7.9Hz); 6.83 (d, 2H, J=7.5 Hz); 10.6 (br, 2H)

(f) 4-Amino-5-(N-methylamino)-2',7'-difluoro-3',6'-dihydroxy-spiro[isobenzofuran-1(3H),9'-[9H]xanthen]-3-one (6: DAF-FM)

DAF-7 (0.94 g, 2.4 mmol) was dissolved in ethanol (200 ml), and the solution was added with methyl iodide and stirred at 80° C. under argon atmosphere for 3 hours. The product was purified by silica gel chromatography and preparative TLC to obtain the title compound (0.15 g, 15%). The compound was further purified by recrystallization from methanol.

$^1$H-NMR (300 MHz, DMSO-$d_6$) δ 2.79 (d, 3H, J=4.6 Hz); 5.32 (q, 1H, J=4.6Hz); 6.05 (s, 2H); 6.23 (d, 1H, J=7.8 Hz); 6.48 (d, 2H, J=11.3 Hz); 6.65 (d, 1H, J=7.8 Hz); 6.83 (d, 2H, J=7.5 Hz); 10.6 (br, 2H)

MS m/z 412(M+)

m.p. 265° C.

EA for $C_{21}H_{14}F_2N_2O_5 \cdot CH_4O$

Calcd.: C, 59.46; H, 4.08; N, 6.31.

Found: C, 59.45; H, 3.78; N, 6.02.

(g) 4,5-Diamino-3',6'-bis(acetyloxy)-2',7'-difluoro-spiro[isobenzofuran-1(3H),9'-[9H]-xanthen]-3-one (7: DAF-FM DA)

Acetic anhydride (52 ml, 0.55 mmol) was added to DAF-FM (94 mg, 0.23 mmol) and $Cs_2CO_3$ (84 mg, 0.26 mmol) suspended in acetonitrile (20 ml), and the mixture was stirred at room temperature for 2 hours. The reaction mixture was concentrated under reduced pressure, and the residue was purified by silica gel chromatography (84 mg, 75%). The product was further recrystallized from 2-isopropanol to obtain the title compound.

$^1$H-NMR (300 MHz, $CDCl_3$) δ 2.34 (s, 6H); 2.93 (s, 3H); 3.40 (br, 1H); 5.05 (s, 2H); 6.48 (d, 1H, J=7.9 Hz); 6.73 (d, 2H, J=10.1 Hz); 6.87 (d, 1H, J=7.9 Hz); 7.09 (d, 2H, J=6.2 Hz)

MS m/z 496(M+)

m.p. 135° C.

EA for $C_{25}H_{18}F_2N_2O_7 \cdot C_3H_8O \cdot 0.1H_2O$

Calcd.: C, 60.23; H, 4.73; N, 5.02.

Found: C, 60.01; H, 4.43; N, 5.00.

(h) 2'',7''-Difluoro-3'',6''-dihydroxy-spiro[1'-methyl-triazolo[4',5':4,5]isobenzofuran-1(3H),9''-[9H]xanthen]-3-one (8: DAF-FM T)

DAF-FM (27 mg, 65 mmol) was dissolved in methanol and bubbled with nitrogen monoxide gas. The solvent was evaporated, and the residue was purified by silica gel chromatography (10% methanol/90% dichloromethane v/v, 0.02% acetate, v/v). The obtained product was dissolved in a small amount of 2 N NaOH aqueous solution, and the solution was adjusted to pH 3-4 with hydrochloric acid. The precipitates were collected by filtration and dried to obtain the title compound (13 mg, 48%).

$^1$H-NMR (300 MHz, acetone-$d_6$) δ 4.50 (s, 3H); 6.69 (d, 2H, J=11.2 Hz); 6.94 (d, 2H, J=7.5); 7.41 (d, 1H, J=8.6); 8.25 (d, 1H, J=8.6Hz); 9.6 (br, 2H)

MS m/z 423 (M+)

m.p. >300° C.

Example 2 pH Characteristics of DAF-FM T

Triazole derivatives prepared by the method disclosed in U.S. Pat. No. 5,874,590 (DAF-2T and DAF-5T, the structures thereof are shown below) and DAF-FM T were dissolved at 1 μM in sodium phosphate buffers adjusted to each of the pH values, and fluorescence intensity was measured. The excitation wavelength and fluorescence wavelength were 495-515 (nm) for DAF-2T, 505-520 (nm) for DAF-5T and 495-515 (nm) for DAF-FMT, respectively. The results are shown in FIG. 1. As a result, pKa of the hydroxyl group was 6.27 for DAF-2T, 4.59 for DAF-5T, and 4.38 for DAF-FMT, respectively, and pKa of the proton of the triazole ring was 7.94 for DAF-2T and 7.41 for DAF-5T. As for DAF-FM T, a dissociable proton was not present in the triazole ring, and therefore the compound was not influenced by pKa and it gave a constant fluorescence intensity at pH 5.8 or higher.

Example 3

Photostability of DAF-FM T

Figure 2:
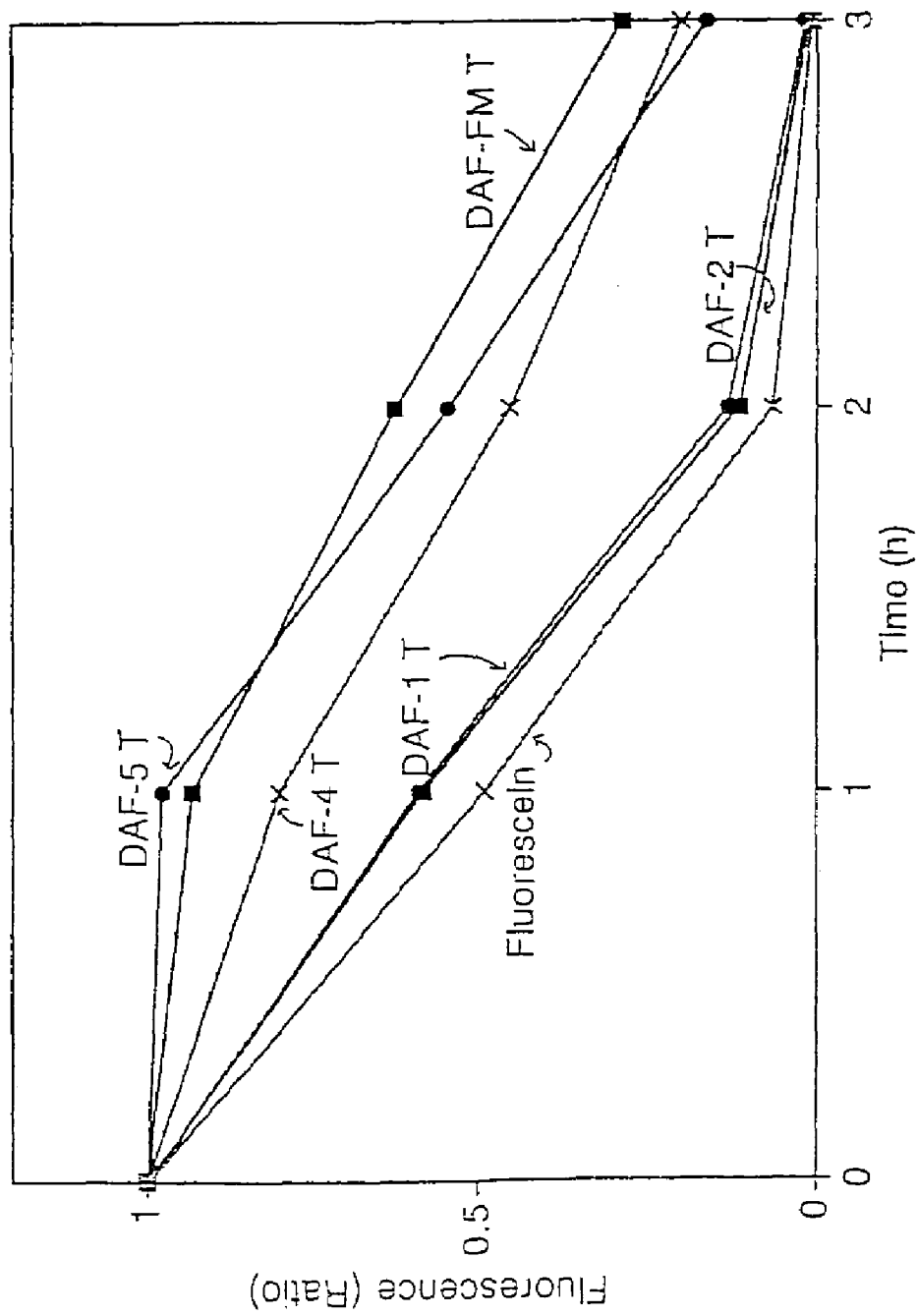
FIG. 2 shows photostability of the triazole derivatives disclosed in U.S. Pat. No. 5,874,590 (DAF-1T, DAF-2T, DAF-4T and DAF-5T) and DAF-FM T.

Photostability of the triazole derivatives produced by the method disclosed in U.S. Pat. No. 5,874,590 (DAF-1T, DAF-2T, DAF-4T and DAF-5T, the structures thereof are shown below) and DAF-FM T was tested by direct irradiation with sunlight. The dyes were each dissolved in 0.1 M sodium phosphate buffer (pH 7.4) at a concentration of 1 μM, and the solution was put into vials and exposed to direct sunlight under fine weather for a certain period of time. Samples were collected from the solutions, and fluorescence intensity was measured and compared with respective initial values. The results are shown in FIG. 2. DAF-FM T of the present invention had higher photostability than the other triazole compounds.

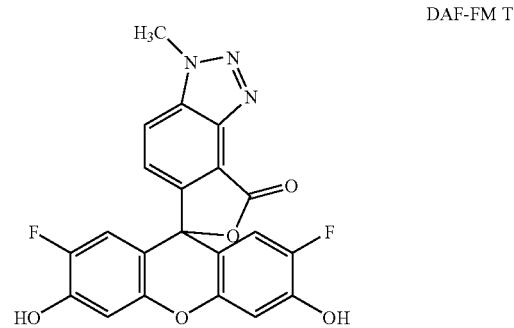

DAF-FM T

-continued

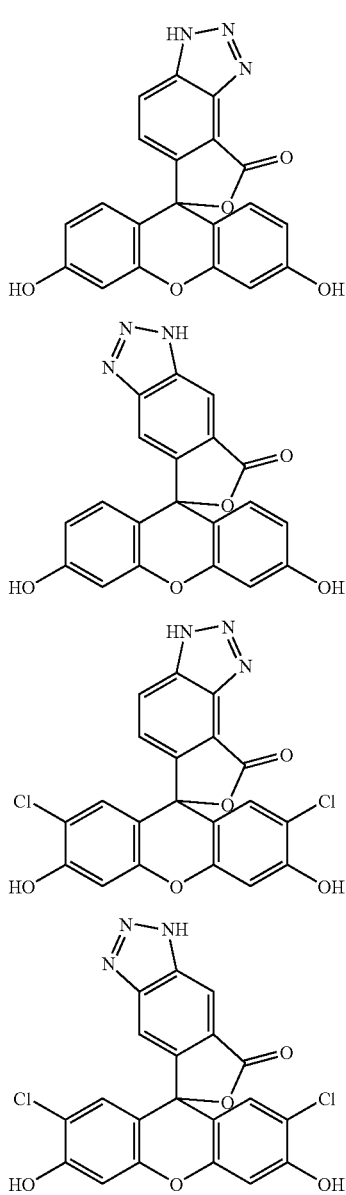

DAF-1T

DAF-2T

DAF-4T

DAF-5T

Example 4

Measurement of Extracellularly Produced Nitrogen Monoxide

Figure 3:
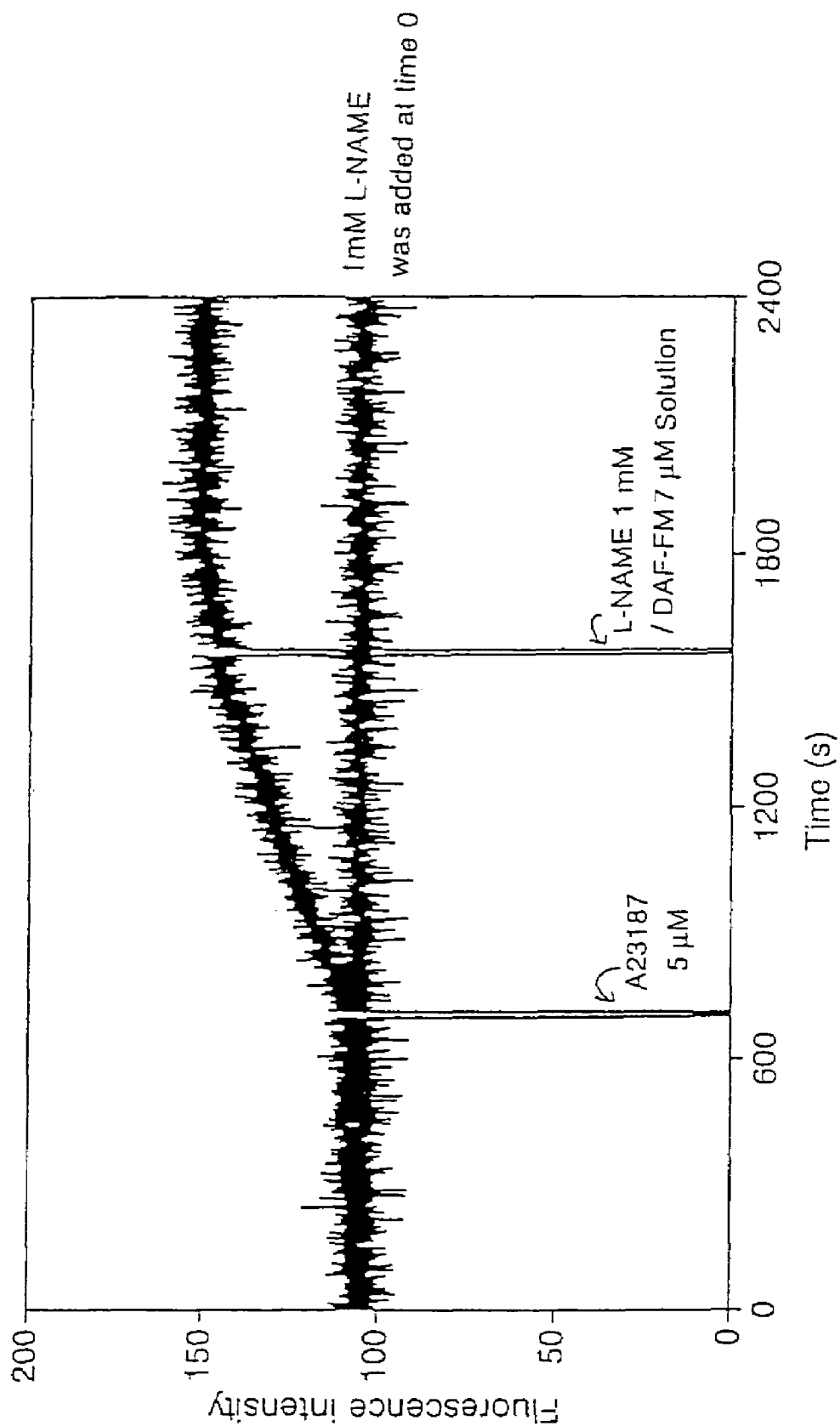
FIG. 3 shows results of measurement of nitrogen monoxide formed extracellularly by bovine aorta endothelial cells.

Bovine aorta endothelial cells were cultured, and the cells were removed with trypsin and collected by centrifugation, and then suspended in 2 ml of PBS(+) in which DAF-FM (7 µM) was dissolved. These cells were transferred to a cell for fluorescence measurement, and fluorescence intensity was measured (Ex.: 500 nm, Em.: 515 nm) at 37° C. with stirring. The cells were stimulated with a calcium ionophore A23187 during the measurement so that the cells generated nitrogen monoxide. The results are shown in FIG. 3. As control experiments, an inhibitor of nitrogen monoxide synthetase was added after the above measurement, or alternatively, the measurement was performed in the presence of the inhibitor from the beginning. The cease of increase of fluorescence was observed, which verified that the increase of fluorescence intensity was caused by nitrogen monoxide.

Example 5

Imaging of Intracellular Nitrogen Monoxide

Figure 4:
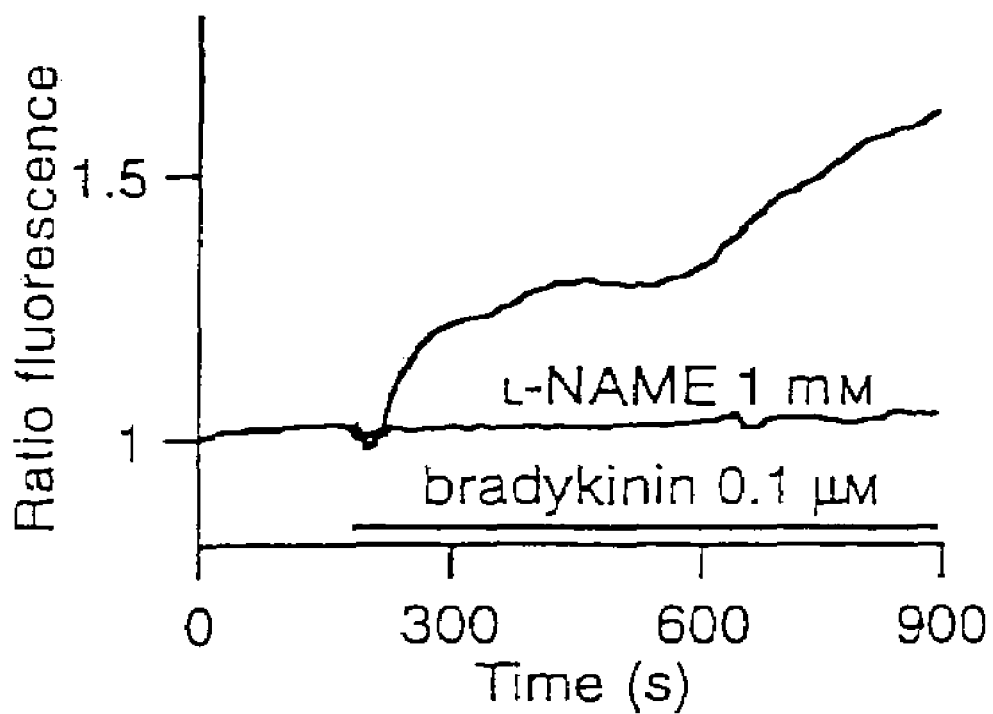
FIG. 4 shows results of measurement of nitrogen monoxide formed intracellularly by bovine aorta endothelial cells.

Bovine aorta endothelial cells were cultured on a dish for imaging. The cell supernatant was replaced with a solution of DAF-FM DA (10 µM) in PBS(+) (containing 0.2% DMSO) to load the dye on the cells at 37° C. for about 1 hour. After the cells were washed, the PBS(+) was replaced with PBS(+) not containing the dye, and the cells were observed by a fluorescence microscope provided with an excitation filter (490 nm), dichronic mirror (505 nm), and barrier filter (515 nm (long pass)). The measurement was performed in an incubator kept at 37° C. Imaging interval was set to 10 seconds, and images taken by a cooled charge-coupled device camera were analyzed by an image analyzer. The results are shown in FIG. 4. The results shown in the figure are indicated by averages of relative fluorescence intensities of seven arbitrary cells based on fluorescence intensities at the start of the measurement obtained. The fluorescence intensity was increased by stimulation with bradykinin, and the increase was suppressed in the presence of the inhibitor of nitrogen monoxide synthetase, which indicates that intracellular nitrogen monoxide was successfully imaged. The data of imaged fluorescence intensity were obtained in a similar manner.

INDUSTRIAL APPLICABILITY

The compounds of the present invention are useful as an agent for nitrogen monoxide measurement. The compounds of the formula (I) of the present invention have a property of efficiently reacting with nitrogen monoxide to give the fluorescent compounds of the formula (II). The compounds of the formula (II) have characteristic features in that they emit strong fluorescence by irradiation of excitation light having a long wavelength which does not cause damages to living tissues and cells, and that their fluorescence intensity is not substantially influenced by pH and they have excellent photostability.

What is claimed is:

1. A method for measuring nitrogen monoxide in a sample comprising:
    combining a sample comprising nitrogen monoxide with a compound of formula I',
    reacting the compound with nitrogen monoxide to form a reaction product having fluorescent properties and measuring a fluorescence intensity of the reaction product in the sample;
  wherein formula I' is:

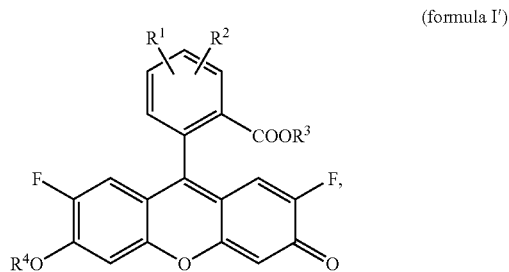

(formula I')

and wherein $R^1$ and $R^2$ represent amino groups, provided that at least one of $R^1$ and $R^2$ represents a mono($C_{1-6}$alkyl)-substituted amino group; and $R^3$ and $R^4$ independently represent hydrogen or an acyl group.

2. The method according to claim 1, wherein the nitrogen monoxide is generated by nitrogen monoxide synthetase.

3. The method according to claim 1, wherein the sample comprises living tissue comprising cells having an extracellular and an intracellular space.

4. The method according to claim 3, wherein the compound of formula I' is present in the intracellular space.

5. The method according to claim 4, wherein the measurement of fluorescence intensity is an indicator of intracellular nitrogen monoxide synthetase activity.

6. The method according to claim 3, wherein the at least one compound is present in the extracellular space and the measurement of fluorescence intensity is an indicator of extracellular nitrogen monoxide activity.

7. The method according to claim 3, wherein at least two compounds of formula I' are simultaneously measuring nitrogen monoxide presence in the intracellular and extracellular space.

8. The method according to claim 1, wherein measuring nitrogen monoxide comprises at least one of detecting the presence of, and determining a concentration of, nitrogen monoxide.

9. The method according to claim 1, wherein the method comprises adding an oxygen source to the sample.

10. A method of measuring an inhibitory activity of a test compound on the activity of a nitrogen monoxide synthetase comprising:
    adding a compound of formula I' to at least one sample comprising nitrogen monoxide synthetase; and
    comparing fluorescence intensity produced by the at least one sample in the presence and absence of a test compound;
wherein formula I' is:

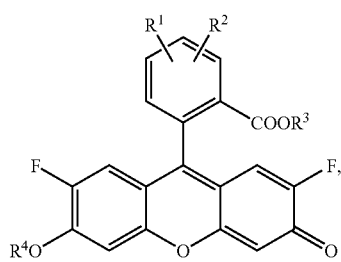

(formula I')

wherein $R^1$ and $R^2$ represent amino groups, provided that at least one of $R^1$ and $R^2$ represents a mono($C_{1-6}$alkyl)-substituted amino group; and $R^3$ and $R^4$ independently represent hydrogen or an acyl group.

11. The method according to claim 10, comprising adding a compound of formula I' to at least two samples comprising nitrogen monoxide synthetase, wherein at least one sample includes the test compound and wherein at least one sample excludes the test compound.

12. The method according to claim 11, comprising adding a compound of formula I' to at least three samples comprising nitrogen monoxide synthetase, wherein at least two samples include the test compound at different concentrations.

13. The method according to claim 10, wherein the method comprises adding an oxygen source to the sample.

14. A method for screening a library of test compounds for inhibitory activity of nitrogen monoxide synthetase comprising:
    preparing at least two samples comprising nitrogen monoxide synthetase, wherein one sample is designated as a control;
    combining at least one sample of nitrogen monoxide synthetase with at least one test compound of the library;
    adding a compound of formula I' to each reaction;
    measuring a fluorescence intensity of each sample; and
    comparing the fluorescence intensity of each sample with the fluorescence intensity of the control reaction;
wherein formula I' is:

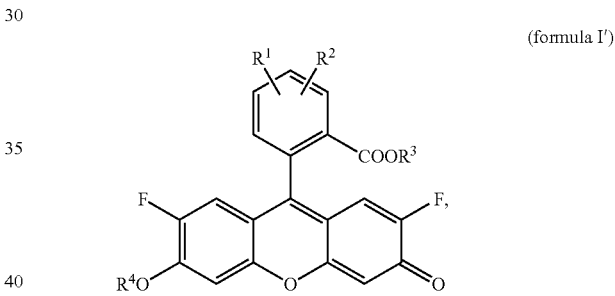

(formula I')

wherein $R^1$ and $R^2$ represent amino groups, provided that at least one of $R^1$ and $R^2$ represents a mono($C_{1-6}$alkyl)-substituted amino group; and $R^3$ and $R^4$ independently represent hydrogen or an acyl group.

15. The method according to claim 14, wherein the method comprises adding an oxygen source to the sample.

16. The method according to claim 14, further comprising repeating the method for at least one different concentration for at least one test compound.

* * * * *